United States Patent [19]

Kaneko et al.

[11] Patent Number: 5,218,757
[45] Date of Patent: Jun. 15, 1993

[54] TAPERED CARBON MICROELECTRODE AND PROCESS FOR PRODUCTION THEREOF

[75] Inventors: Hiroko Kaneko; Masahiro Yamada; Yukifumi Shigematsu; Wataru Mizutani, all of Ibaraki; Akira Negishi, Chiba; Takamasa Kawakubo; Yoshihisa Suda, both of Gunma, all of Japan

[73] Assignees: Agency of Industrial Science and Technology; Mitsubishi Pencil Kabushiki Kaisha, both of Tokyo, Japan

[21] Appl. No.: 722,545

[22] Filed: Jun. 25, 1991

[30] Foreign Application Priority Data

Jul. 16, 1990 [JP] Japan ................................ 2-185250

[51] Int. Cl.[5] ............................................ G01N 27/26
[52] U.S. Cl. ........................................ 29/855; 29/825; 29/854; 29/885; 264/29.6; 264/29.5; 264/29.1; 204/416
[58] Field of Search ............... 264/29.6, 29.5, 29.1; 29/885, 825; 204/416

[56] References Cited

U.S. PATENT DOCUMENTS

| | | | |
|---|---|---|---|
| 4,822,538 | 4/1989 | Yoshida et al. | 264/29.6 |
| 4,950,443 | 8/1990 | Kawakubo et al. | 264/29.5 |
| 5,004,511 | 4/1991 | Tamura | 264/29.6 |
| 5,110,516 | 5/1992 | Yoshida | 264/29.6 |

Primary Examiner—John Niebling
Assistant Examiner—Bruce F. Bell
Attorney, Agent, or Firm—Darby & Darby

[57] ABSTRACT

A tapered carbon microelectrode is produced by extruding an organic material or a composition composed of crystalline carbon fine powder and an organic binder into a thin rod form, carbonizing said rod by calcining to produce a pure carbon thin rod, soaking the resulting thin rod as an anode in an electrolytic solution, gradually pulling up the thin rod while electrochemically oxidizing the tip portion of the thin rod. Then a lead wire is connected with the thick portion of the thin rod followed by coating all the surface except the conically sharp tip portion.

The tapered carbon electrode can be used for various electrochemical measurements and scanning tunneling microscope.

4 Claims, 2 Drawing Sheets

STM IMAGE 4nm 4nm

Blank Current (1M KCl)

$\phi$ : 50 $\mu$m
$\mathrm{I}\ 2\mu A$  1 : 2mm
V : 0.5V/S

1mM Fe(CN)$_6^{4-}$ in 1M KCl $\phi$ : 50 $\mu$m
$\mathrm{I}\ 2\mu A$  1 : 2mm
V : 0.5V/S

TAPERED CARBON MICROELECTRODE AND PROCESS FOR PRODUCTION THEREOF

BACKGROUND OF THE INVENTION

1. Field of the Invention

The present invention relates to a tapered carbon mecroelectrode and a process for producing said tapered carbon microelectrode.

More particularly, the present invention relates to a tapered carbon microelectrode for voltammetry, electrochemical detectors, probes and electrode for STM (Scanning Tunneling Microscope) and related method, sensors for environmental analysis, sensors for pathological test, probe electrodes for detection used for living body system, food and the like where harmlessness and innoxiousness are strictly required, and the like, and a process for the production thereof.

2. Description of Related Art

Electrochemical detection methods such as voltammetry, high performance liquid chromatography, sensors and the like are widely used for highly selective and highly sensitive measurements.

Therefore, the methods are often used for analysis and evaluation of clinical living body samples and environmental samples containing components to be measured only in extremely small amounts and many compounds coexisting therewith.

An important member determining the performance of the electrochemical detector is a working electrode, and the kind of the selected working electrode material largely influences on the kinds of substances which can be measured, sensitivity, selectivity, and possibility of quantitative analysis.

Heretofore, as the electrodes for electrochemical measurement, there have been investigated various mercury electrodes, platinum, gold, copper, silver, carbon (glasslike carbon) (GC), carbon fiber (CF), carbon paste (CP), highly oriented pyrolytic graphite (HOPG) and the like.

Among them, mercury electrode and GC are mainly used as an electrode for polarography and an electrode for an electrochemical detector, respectively.

However, mercury is not desirable from the standpoint of environmental protection due to its poisonous property, and thereby nonpoisonous and good electrodes in place of mercury electrode are in demand. Though a GC electrode is composed of nonpoisonous carbon, it is difficult to treat the surface of the electrode, reproducibility of measurement result is not good and further, its use has problems. Other metal electrodes are liable to poison a living body system and are expensive, and the electrochemical characteristics have both merits and demerits.

Some of the present inventors found that a composite carbon material GRC (graphite reinforcement carbon) which had been used as a mechanical pencil lead exhibited excellent characteristics as an electrode for electrochemical measurements and succeeded in using the lead as the electrode and proposed a graphite composite carbon electrode (GRC) which can be easily used (Japanese Patent Application No. Sho 63-78698) as the electrode.

Further, they succeeded in making the GRC thin (Japanese Patent Application No. Hei 1- 250772).

Recently it is very important to obtain physiological information at a local portion of a living body, for example, nerve cell system in vivo and in situ by means of an electrode for electrochemical measurement.

The above mentioned thin GRC has been also produced for such purpose. That is, it is demanded to measure the change with time of responses from nerve cells and secreted amounts of chemical transmitters from nerve cells by placing an electrode in the vicinity of the nerve cells in the living body to be measured or directly pricking an electrode into a living body to stimulate directly the nerve so as to give a physical, chemical or electrical stimulus.

Therefore, a very thin electrode nonpoisonous to cells (on the order of $\mu$m) is necessary.

The thin GRC in one of the above-mentioned prior Japanese Patent Applications can be sufficiently used for this purpose and it has been already shown that a separate quantitative analysis of dopamine and vitamin C.

However, the GRC is anyhow so thin that the electric resistance is somewhat high and the mechanical strength is not sufficient though depending on the place to be pricked with the GRC and thereby a tougher thin electrode is demanded.

A research on fabricating an electrode by using a thin carbon fiber in a manner similar to above has been conducted, but it is difficult to find electrodes of good reproducibility, and further, the carbon fiber electrodes are not tough and the strength is almost similar to that of the thin GRC.

Probes having a thin tip portion have been recently used in STM which is a new field of application of electrode for electrochemical measurements and the related technical fields since electric current measurements and cyclic voltammetric measurements are conducted therein.

However, any materials now available are poor in reproducibility so that inexpensive electrodes for STM of good reproducibility are in demand.

STM measurements have been recently explosively developed and therefore, a microprobe and a microelectrode are very important since it influences the performance of a STM apparatus.

The advantage of using carbon microelectrodes as probes for STM is not only the property that carbon rod can be thinned, but also no electrochemical problem caused between different materials since a clean graphite plate (for example, HOPG) is often used as a substrate for bearing a sample to be measured and simultaneously functioning as a counter electrode and a tapered carbon microelectrode in which the atom of the probe portion, that is, the end portion of graphite crystal and amorphous carbon tip portion, is the same kind as that of the counter electrode-substrate. This advantage is also available in the present invention.

The present inventors have intended to solve the above-mentioned problems of electrode materials. A carbon microelectrode of Japanese Patent Application No. Hei 1- 250772 has the following features i) - vii).

i) A carbon microelectrode capable of applying any of electric current, voltage, and mechanical stimuli to a living body and the size of the functioning portion being of an order of cell.

ii) A carbon microelectrode which does not contaminate the system to be measured and even if it remains in a living body, it is not harmful, and it can be used for examining food.

iii) A carbon microelectrode having a mechanical strength sufficient to prick a living body and food for an electrochemical detection as to a microportion or microamount.

iv) Little fluctuation of electrode characteristics, good reproducibility of data, and reliable measurement.

v) Any special pretreatment is not necessary, and at most an electrochemical pretreatment is enough to measure stably an electrode reaction.

vi) Low cost and disposable.

vii) A carbon microelectrode having low electric resistance (good electric conductivity), high prick strength (toughness) and a very strong stem (hardly broken) as compared with carbon fiber electrodes (CF) and thin GRC electrodes.

The present inventors have intended to produce a carbon microelectrode having the above-mentioned features i) - vii) in addition to solving the above-mentioned problems of electrode materials.

In general, essential conditions for a voltammetric electrode are as shown below.

i) Wide polarized potential domain and small blank current.

ii) Good reproducibility, and repeated use is possible.

iii) Having an electrode reaction activity.

iv) Individual electrodes do not have different characteristics from one another.

v) Impurities are so little that electrode reaction is not disturbed.

vi) Theoretical interpretation is possible.

vii) Handling and pretreatment are easy.

According to prior filed Japanese patent applications, that is, Japanese Patent Application Nos. Sho 63-78698, Hei 1-250772 and Hei 2-1051, carbon microelectrodes are disclosed which can be sufficiently used directly. However, in the case of using for measuring potential only, they have undesirably high electric resistance and furthermore, the mechanical strength is not enough to prick a somewhat hard matter so as to measure and apply an electric stimulus. The shape of those electrodes are not appropriate when they are used as an STM probe electrode which desirably has a shape such that the tip portion only is to be very thin. In addition, there has been demanded an electrode having a thick and strong upper portion while only the tip portion has a thinness enough for the purpose of electrochemical measurement.

If the above-mentioned problems can be solved, the following conditions also can be satisfied.

viii) Electric resistance is lowered.

ix) Mechanical strength required for prick is elevated.

x) The stem portion is strengthened.

xi) The length and diameter of the microcylinder portion at the tip and the length of the taper portion can be optionally controlled.

xii) A desired portion of the above-mentioned electrode having such irregular shape can be sufficiently insulated.

The present inventors have intensively researched so as to attain the characteristics viii) to xii) as well as i) to vii), in addition to solving the above-mentioned problems and producing a carbon microelectrode having the previously mentioned features i) - vii). As a result, the present invention has been completed.

SUMMARY OF THE INVENTION

An object of the present invention is to provide a tapered carbon microelectrode free from the above-mentioned drawbacks of the electrode materials.

Another object of the present invention is to provide a tapered carbon microelectrode having a mechanical strength, in particular, a prick strength.

A further object of the present invention is to provide a tapered carbon microelectrode having a low electric resistance and a prick strength.

Still another object of the present invention is to provide a tapered carbon microelectrode for STM and the related method.

A still further object of the present invention is to provide a process for producing a tapered carbon microelectrode capable of easily controlling the taper of the tip portion.

According to one aspect of the present invention, there is provided a tapered carbon microelectrode produced by (i) extruding an organic material itself or a composition prepared by highly dispersing and compounding crystalline carbon fine powder with an organic material as a binder into a desired thin rod form, (ii) calcining the product thus extruded in an inert atmosphere or in a non-oxidizing atmosphere up to an elevated temperature, (iii) thereby carbonizing the organic material itself or the organic binder contained in the composition to produce a pure carbon thin rod, (iv) soaking the resulting carbon thin rod as an anode in an electrolytic solution, at near the oxygen evolution potential, (v) gradually pulling up the carbon thin rod while subjecting the tip portion of the carbon thin rod to electrochemical oxidation to form a conically sharp tip portion having an extremely small diameter, (vi) then connecting a lead wire with the thick end portion of the carbon thin rod, and (vii) coating with an insulating material all the surface of the carbon thin rod except a desired portion at the conically sharp tip portion having an extremely small diameter.

According to another aspect of the present invention, there is provided a method for producing a tapered carbon microelectrode which comprises (i) extruding an organic material itself or a composition prepared by highly dispersing and compounding crystalline carbon fine powder with an organic material as a binder into a desired thin rod form, (ii) calcining the product thus extruded in an inert atmosphere or in a non-oxidizing atmosphere up to an elevated temperature, (iii) thereby carbonizing the organic material itself or the organic binder contained in the composition to produce a pure carbon thin rod, (iv) soaking the resulting carbon thin rod as an anode in an electrolytic solution, at near the oxygen evolution potential, (v) gradually pulling up the carbon thin rod while subjecting the tip portion of the carbon thin rod to electrochemical oxidation to form a conically sharp tip portion having an extremely small diameter, (vi) then connecting a lead wire with the end portion of the carbon thin rod, and (vii) coating with an insulating material all the surface of the carbon thin rod except a desired portion at the conically sharp tip portion having an extremely small diameter.

DESCRIPTION OF THE PREFERRED EMBODIMENTS

Figure 1:
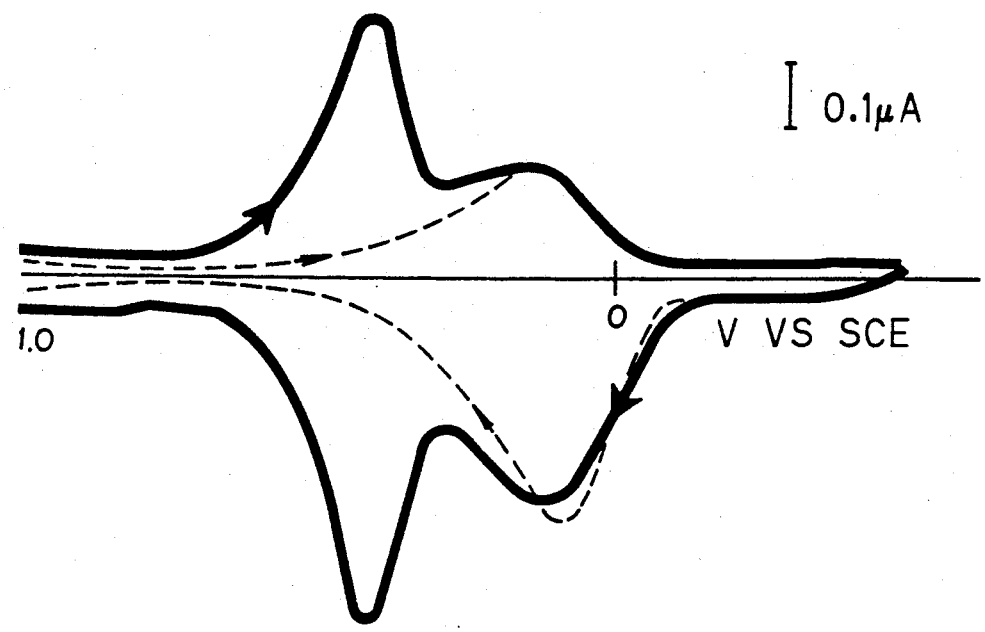
FIG. 1 shows a result of measurement of differential pulse voltammograms (D.P.V. curves) by means of a tapered carbon microelectrode produced in Example 1 (infra).

The tapered carbon microelectrode of the present invention may be produced as shown below.

An organic material itself or a composition prepared by highly dispersing and compounding crystalline carbon fine powder with an organic binder is extruded into a desired thin rod form and then calcined in an inert atmosphere or in a non-oxidizing atmosphere up to an elevated temperature to carbonize the organic material itself or the organic binder contained in the composition to form a pure carbon thin rode.

A desired length of the carbon thin rod thus obtained is soaked in an electrolytic solution as an anode and oxidation is started at a potential region of 1 V vs. saturated calomel electrode (SCE). The potential and the pulling-up speed are controlled so that a conical form having a desired taper may be produced, and as a result, the tip portion is finished to a desired tip diameter.

The thick end of the resulting tapered carbon thin rod is electrically connected with a lead wire by means of an electroconductive silver paste cemment and then the whole surface thereof is covered with an insulating material, if desired, followed by removing the insulating film at the thin end of the tapered carbon thin rod to expose said end portion. Thus a tapered carbon microelectrode is completed.

What are meant by "organic materials and organic binders" are organic materials capable of effectively forming carbonized materials as residue when calcined in an inert atmosphere or in a non-oxidizing atmosphere. Said organic materials are, for example, organic high polymers, monomers thereof, oligomers, tars, pitches, dry distillation pitches, thermoplastic resins, initial stage polymers of thermosetting resins and the like. These organic materials may be used alone or in combination.

More in detail, the organic high polymers include natural organic high polymers such as lignin, cellulose, tragacanth, gum arabic, natural rubber and derivatives thereof, compounds containing condensed polycyclic aromatic groups in the fundamental structure of the molecule such as saccharides, chitin, chitosan and the like, and synthetic high polymers, excluding thermoplastic resins and thermosetting resins as mentioned later, such as naphthalene sulfonic acid-formaldehyde condinsate, dinitronaphthalene, pyrene, pyranthrone, violanthrone, benzoanthrone and the like, indanthrene vat dye and intermediates thereof.

The thermoplastic resins include ordinary thermoplastic resins such as poly(vinyl chloride), polyacrylonitrile, poly(vinylidene chloride), chlorinated poly(vinyl chloride), poly(vinyl acetate), poly(vinyl alcohol), poly(vinylpyrrolidone), ethyl cellulose, carboxymethyl cellulose, vinyl chloride-vinyl acetate copolymer and the like, and heat resistant thermoplastic resins such as polyphenylene oxide, poly-p-xylene, polysulfone, polyimide, polyamidoimide, polybenzimidazole, polyoxadiazole and the like.

The thermosetting resins include phenolic resins, furan resins, epoxy resins, xylene resins, COPNA resins (Condensed Polynuclear Aromatic resin, available as "SK Resin" from Sumitomo Kinzoku Kogyo K.K.) and the like.

As the thermosetting resins, there are preferably used those capable of being fluidified by heating simultaneously with forming crosslinking between molecules resulting in formation of a three dimensional structure by heating and giving a high carbon residue yield without any particular carbon precursor producing treatment.

The pitches include petroleum pitch, coal tar pitch, asphalt, and dry distillation products (treated at a temperature of 400° C. or lower) from hydrocarbon compounds such as pitches, synthetic resins and the like.

As the crystalline carbon fine powder compounded with the organic binder according to the present invention, a glass-like matter produced by carbonizing the organic material itself may be used to attain the object of the present invention, but for purposes of effecting the electrode reaction better, it is preferable to prepare a composite carbon material having an oriented system such that end surfaces of highly developed graphite crystals are arranged to be perpendicular to the electrode surface.

Therefore, as the crystalline carbon fine powder, there are preferably used graphite whisker, highly oriented pyrolytic graphite (HOPG), kish graphite, natural graphite having developed crystal, artificial graphite and the like.

Preferable particle size of the crystalline carbon fine powder varies depending on the diameter of electrode to be used, but is usually several μm or less.

The amount of the crystalline carbon fine powder to be compounded varies depending on the type of the organic binder to be compounded with and the diameter of the contemplated electrode, but is usually 5–80% by weight, preferably 40–60% by weight based on the organic thin rod composition before carbonization (green composition).

It is important for preparing the crystalline carbon composite organic thin rod before calcination (green thin rod) to effect the following steps, i.e. compounding the above-mentioned organic binder with crystalline carbon fine powder accordingly at an appropriate ratio depending on the purpose, dispersing the powder sufficiently by means of Henschel mixer or the like, if desired, adding plasticizers, solvents or the like, cleaving graphite crystals in the organic binder by means of a kneader capable of applying a high shearing stress such as a pressurized kneader, two rolls and the like, and thereby causing a mechanochemical reaction to effect a sufficient mixing and dispersion.

The resulting mixture is then made into pellets by means of a pelletizer and extruded by a screw extruder to form a thin fod of a desired diameter by extruding and shaping. In this procedure it is preferable to apply stretching to the thin rod so as to improve the characteristics.

Then, for the purpose of maintaining straightness of the fine line, the thin rod is fixed to a supporting frame and treated in an air-oven heated at 180° C. for 10 hours to produce a carbon precursor thin rod material.

The resulting precursor thin rod material is then calcined and carbonized. The calcination and carbonization are preferably carried out by heat treatment in an inert atmosphere or non-oxidizing atmosphere at 500°-1500° C.

More preferably the calcination and carbonization are carried out by heat treatment in an inert atmosphere or non-oxidizing atmosphere at 500°-1000° C. and then graphitization is effected by heating in an inert atmosphere at 2000°-3000° C.

For example, the resulting precursor thin rod material is carbonized by heating up to 1000° C. at a controlled temperature under rising speed in a nitrogen atmosphere and as a result of the calcination, a composite carbon thin rod can be obtained. If desired, the resulting composite carbon thin rod is further subjected to a heat treatment up to 2500° C. in an argon gas phase to graphitize it wholly, depending upon the individual purpose.

As an electrolytic solution used for a wet type electrochemical oxidation according to the present invention, there may be used an aqueous alkaline solution containing potassium hydroxide, sodium hydroxide, calcium hydroxide ammonium hydroxide or the like; a diluted acid prepared by diluting hydrochloric acid, sulfuric acid, perchloric acid, nitric acid, phosphoric acid or the like with pure water, or an aqueous solution of salts thereof such as sodium chloride, potassium chloride, potassium sulfate and the like.

When the material contains a large amount of graphite, it is preferable to use an aqueous solution of the former, i.e. hydroxide, which hardly forms intercalation compounds.

As an insulating material for insulation, there may be used glass, oxides such as $SiO_2$, $Al_2O_3$ and the like, plastics and the like. When the insulating material should be soaked in an electrolytic solution for its use, it is preferable that the material is composed of an anticorrosion resin material such as Teflon, silicone, and the like.

A method for insulation coating can be effected by an ordinary coating procedure in the case of plastics. That is, a spray coating, dipping coating, electrostatic coating or the like is suitable.

In the case of forming a glass insulation coating, a tapered carbon thin rod connected with a lead wire at the thick end portion using a silver paste cement is inserted into and held in a capillary tube of Pyrex glass, and then both ends of the Pyrex glass capillary tube are fixed to respective pulling terminal of a puller for fabricating glass capillary tubes. The center portion of the Pyrex glass capillary tube is uniformly heated to plasticize the tube simultaneously with pulling the puller, and thereby a glass film is formed while the carbon thin rod is kept to be held.

The resulting product is cut at the center portion to expose one end of the carbon thin rod and a desired electrode is accomplished.

In the tapered carbon microelectrode, the diameter of the thick end portion of the tapered carbon thin rod is preferably 5 mm-0.1 mm and that of the thin end portion is 0.1 mm or less.

As described above, the tapered carbon microelectrode having a very thin tip portion of the present invention can provide an electrode for STM for which a carbon electrode has not yet been used and a good carbon microelectrode for in situ measurements.

That is, the tapered carbon microelectrode according to the present invention has good characteristics of the carbon microelectrode of the prior applications and, in addition, has a low electric resistance and a high prick strength. Said tapered carbon microelectrode can be made into cylindrical microelectrodes and conical microelectrodes of a desired length and disc microelectrodes having a desired diameter, and electrodes having a strong supporting portion can be obtained.

In addition, the angle of the tapered portion at the end of the electrode can be easily controlled. Since the starting material for the electrode can be produced under a full quality control, a large amount of the electrodes having stable characteristics can be supplied at a low cost. As a result, a variety of electrodes for measurement having excellent characteristics as mentioned above can be supplied for various uses.

The invention is now more particularly described with reference to the following examples which are for the purpose of illustration only and are intended to imply no limitation thereon.

EXAMPLE 1

As a material for a carbon thin rod for electrodes, a composition (100% by weight) composed of a chlorinated poly(vinyl chloride) (T-742, trade name, manufactured by Nihon Carbide Co.) (60% by weight) and kish graphite fine powder (KH, trade name, manufactured by Kowa Seiko Co.) (40% by weight) was used and a plasticizer, diallyl phthalate monomer, (25% by weight based on the composition) was added thereto.

The resulting mixture was dispersed by using a Henschel mixer and then sufficiently kneaded repeatedly by means of two rollers for mixing at a surface temperature of 120° C. until the graphite crystals were cleaved in the chlorinated poly(vinyl chloride) resin as a matrix to become near a noncoagulated particle state. As a result, a mechanochemical reaction was induced and the sheet-like composition thus dispersed was pelletized by a pelletizer to produce a composition for shaping. The resulting pellets were extruded at a shaping temperature of 130° C. by a screw type extruder with a die having a port of 0.7 mm in diameter while deaerating and the extruded material was fixed to a frame and oxidized by air for 10 hours in an air oven heated to 180° C. to produce a carbon precursor.

Then, the resulting carbon precursor was heated in nitrogen gas up to 500° C. at a temperature rising speed of 10° C./hour, from 500° C. to 1000° C. at a temperature rising speed of 50° C./hour, kept at 1000° C. for 3 hours, and then allowed to cool resulting in completion of the calcination. Thus a carbon thin rod for electrode of 0.5 mm in diameter was obtained. The carbon thin rod was cut into a length of 50 mm to form a material for processing to produce a tapered carbon thin rod.

As an electrolytic solution used for a wet type electrochemical oxidation, a 3M (mol $dm^{-3}$) potassium hydroxide was used and the carbon thin rod as a raw material was used as an anode, and the length of 2 mm of the tip portion was soaked in the electrolytic solution. A potential of 2.2 V vs. SCE was applied thereto to effect oxidation while pulling up the electrode at a speed of 0.1 mm/min. By this treatment for 10 min. the tip portion is shaped into a conical form and the tip diameter was finished to 10 μm.

The thick end of the resulting tapered carbon thin rod was electrically connected with a lead wire by using a silver paste cement and the whole surface was coated with a 15% solution of a glass resin (GR - 100, trade name, manufactured by Showa Denko K.K.) in ethanol, and dried to form an insulating coat. The member thus coated was inserted into a capillary tube of Pyrex glass (0.5 mm in inner diameter, 1 mm in outer diameter) and both ends of the glass tube were fixed to pulling terminals of a puller.

The center portion (5 mm long) of the glass tube was heated to plasticize said portion, and the puller was actuated at a stroke to bring the glass tube wall into close contact with the tapered carbon thin rod. Finally the central portion of the glass tube was cut to expose the carbon surface from the insulating coat resulting in completion of a tapered carbon microelectrode.

The resulting tapered carbon microelectrode was used for detecting dopamine in the presence of vitamin C.

Dopamine is a kind of catecholamines which are neurotransmitters secreted from nerve cells and is an unstable substance which is very liable to be oxidized. Therefore, in the case of a solution, vitamin C is added thereto as a stabilizer and, in a living system, vinamin C often coexists.

In view of the foregoing, it was tried to detect simultaneously dopamine and vitamin C dissolved in Ringer's solution. FIG. 1 shows a result of measurement of differential pulse voltammograms (D.P.V. curves) by means of the tapered carbon microelectrode obtained in this Example 1.

The length of 1.8 mm (20 μm in diameter) of the tip portion of the tapered carbon microelectrode was dipped in Ringer's solution mainly composed of a physiological salt solution in which 1 mM dopamine and 10 mM of vitamin C were contained, and platinum and a saturated calomel electrode were used as a counter electrode and a reference electrode, respectively.
The sweep rate was 10 mV/S and the pulse width was 0.5 sec. The broken line is a D.P.V. curve for vitamin C only while the solid line is a D.P.V. curve for coexistence of both of them.

As a result, it is clear that the separate detection of both of them is sufficiently possible by means of the tapered carbon microelectrode.

EXAMPLE 2

As a material for a carbon thin rod for electrode, a mixture of a chlorinated poly(vinyl chloride) resin (T-742, trade name, manufactured by Nihon Carbide Co.) (100% by weight) and diallyl phthalate monomer (30% by weight based on the weight of the chlorinated poly(vinyl chloride) resin) as a plasticizer was used to prepare pellets. The pellets were extruded at a shaping temperature of 130° C. by a screw type extruder with a die having a port of 1.0 mm in diameter while deaerating and the extruded material was fixed to a frame in a straight line form and oxidized by air for 10 hours in an air oven heated to 180° C. to produce a carbon precursor. The carbon precursor was then calcined in a way similar to Example 1 to produce a carbon thin rod for electrode of 0.5 mm in diameter.

The carbon thin rod was cut into a length of 50 mm to be used as a material for processing to produce a tapered carbon thin rod followed by treating the material by an electrochemical oxidation in a manner similar to Example 1 to finish the tip to a diameter of 10 μm.

The thick end of the resulting tapered carbon thin rod was electrically connected with a lead wire by using a silver paste cement. The resulting member was inserted into a capillary tube of Pyrex glass (0.5 mm in inner diameter, 1 mm in outer diameter) and both ends of the glass tube were fixed to pulling terminals of a puller.

The center portion (5 mm long) of the glass tube was heated to plasticize said portion, and the puller was actuated at a stroke to bring the glass tube wall into close contact with the tapered carbon thin rod. Finally, the central portion of the glass tube was cut to expose the carbon surface from the insulating coat resulting in completion of a tapered carbon microelectrode.

Figure 2A:
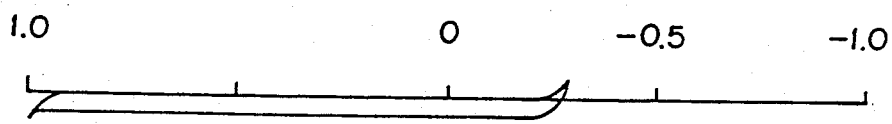
FIG. 2A shows a result of measuring a blank current by dipping the length of 2 mm at the tip portion of the tapered carbon electrode produced in Example 2 (infra) in 1M KCl.
Figure 2B:
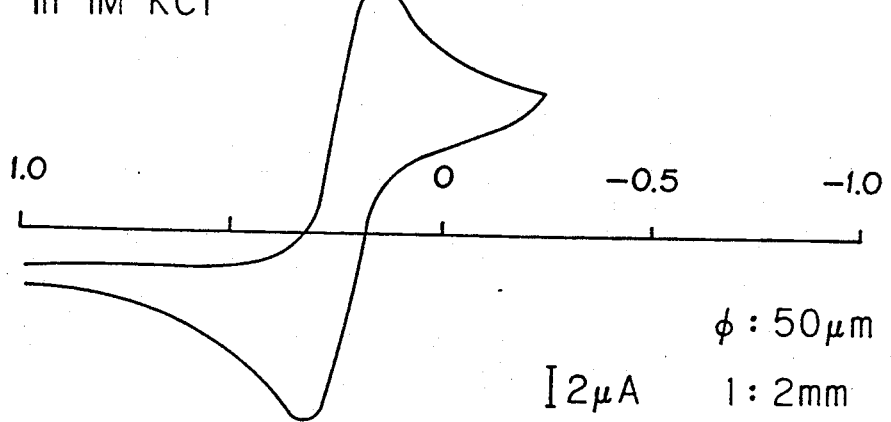
FIG. 2B shows a C-V curve voltammograms obtained by effecting a redox reaction of ferrocyanide ion in a 1M KCl - 1 mM Fe(CN)$_6^{4-}$ system.

By means of the resulting electrode, a blank current was measured in 1 M aqueous KCl, and a redox reaction of ferrocyanide ion was conducted in a 1 M KCl - 1 mM $Fe(CN)_6^{4-}$ system The resulting I - V curve is shown in FIG. 2. The S/N (signal / noise) ratio was high and a good electrode reaction was effected.

EXAMPLE 3

As a raw material for a carbon thin rod, to a composition (100% by weight) composed of a vinyl chloridevinyl acetate copolymer resin (ML, trade name, manufactured by Nihon Zeon Co.) (20% by weight), furan resin initial condensate (VF - 302, trade name, manufactured by Hitachi Kasei K.K.) (40% by weight) and highly crystalline natural graphite fine powder (CSSP - B, trade name, manufactured by Nihon Kokuen K.K.) (40% by weight), was added dibutyl phthalate (25% by weight based on the weight of the composition) as a plasticizer.

The resulting mixture was dispersed by means of Henschel mixer in a way similar to Example 1 and repeatedly kneaded to the fullest extent by means of two rollers for mixing with a surface temperature kept at 70° C. until graphite crystals were cleaved in the matrix resin to become near a noncoagulated particle state.

The resulting sheet-like composition where a mechanochemical reaction had been induced was pelletized by a pelletizer. The composition for shaping thus pelletized was extruded and shaped at 100° C. by a screw extruder provided with a die having a port of 0.50 mm in diameter while deaerating, and then the shaped product was supported and fixed in a straight line form followed by a treatment in an air oven kept at 180° C. for 10 hours to harden completely resulting in formation of a carbon precursor.

Then the carbon precursor was subjected to the same calcination treatment as in Example 1 to produce a carbon thin rod for electrode of 0.35 mm in diameter The carbon thin rod was cut into a length of 30 mm to form a material for processing to produce a tapered carbon thin rod.

A 1 M aqueous solution of sodium hydroxide was prepared as an electrolytic solution for a wet type electrochemical oxidation and the tip portion of 1 mm long of the material for carbon thin rod was soaked in the electrolytic solution and a potential of 2.0 V vs. SCE was applied to start the oxidation, and the treatment was effected for 20 min. without pulling up the electrode to give a conical form and finish the diameter of the tip portion to 1 μm.

The thick end of the resulting tapered carbon thin rod was inserted into a metal pipe of 3.5 mm in inner diameter and electrically connected by using an electroconductive silver paste cement and then the whole surface of the resulting member was covered for insulation with a room temperature-curing type silicone resin except the thin end of the tapered carbon thin rod was exposed in the length of 1 mm. Thus a tapered carbon electrode was completed.

The thick portion of the tapered carbon electrode (0.3 mm in diameter) could be easily fitted to a supporting stand using metal fittings. The tapered tip portion was suitable for a probe and could be used as a probe for STM.

Figure 3:
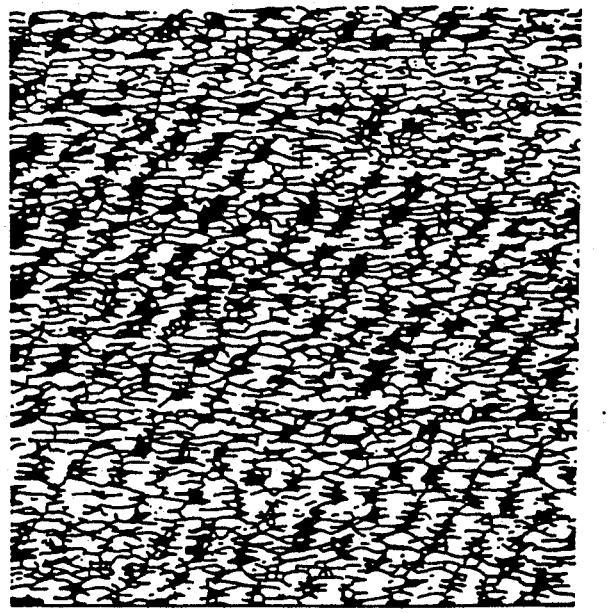
FIG. 3 shows an STM image corresponding to crystal structure of a smooth graphite surface of HOPG obtained by means of a tapered carbon microelectrode produced in Example 3 (infra).

FIG. 3 shows a STM image (corresponding to the crystal structure) of a smooth graphite surface of HOPG observed by using the tapered carbon microelectrode of the present invention as a probe (the probe portion corresponds to the tip portion of the graphite crystal having a tip diameter of about 1 μm). This image corresponds to an area of 4 nm×4 nm and layer-like repetition of graphite was identified.

What is claimed is:

1. A method for producing a tapered carbon microelectrode which comprises
(i) extruding an organic material itself or a composition prepared by highly dispersing and compounding crystalline carbon fine powder with an organic material as a binder into a desired thin rod form,
(ii) calcining the product thus extruded in an inert atmosphere or in a non-oxidizing atmosphere up to an elevated temperature,
(iii) thereby carbonizing the organic material itself or the organic binder contained in the composition to produce a pure carbon thin rod,
(iv) soaking the resulting carbon thin rod as an anode in an electrolytic solution, at near the oxygen evolution potential,
(v) gradually pulling up the carbon thin rod while subjecting the tip portion of the carbon thin rod to electrochemical oxidation to form a conically sharp tip portion having an extremely small diameter,
(vi) then connecting a lead wire with the end portion of the carbon thin rod, and
(vii) coating with an insulating material all the surface of the carbon thin rod except a desired portion at the conically sharp tip portion having an extremely small diameter.

2. The method for producing a tapered carbon microelectrode according to claim 1 in which the calcination and carbonization are carried out by heat treatment in an inert atmosphere or non-oxidizing atmosphere at 500°–1500° C.

3. The method for producing a tapered carbon microelectrode according to claim 1 in which the calcination and carbonization are carried out by heat treatment in an inert atmosphere or non-oxidizing atmosphere at 500°–1000° C. and then graphitization is effected by heating in an inert atmosphere at 2000°–3000° C.

4. The method for producing a tapered carbon microelectrode according to claim 1, in which the electrolytic oxidation for forming a tip portion of the carbon thin rod in a conically tapered form is carried out by soaking a desired length of the tip portion of the carbon thin rod in an electrolytic solution selected from the group consisting of an aqueous alkaline solution containing potassium hydroxide, sodium hydroxide, calcium hydroxide, or ammonium hydroxide, a diluted acid produced by diluting an acid selected from hydrochloric acid, sulfuric acid, perchloric acid, nitric acid, and phosphoric acid with pure water, and an aqueous solution of a salt selected from sodium chloride, potassium chloride, and potassium sulfate, starting the oxidation at an electric potential of 1V vs. SCE (saturated caromel electrode), gradually pulling up the electrode at controlled electric potential and pulling-up speed to produce a conical form with a desired taper.

* * * * *